US00PP11035P

United States Patent [19]

Mowrey et al.

[11] Patent Number: Plant 11,035

[45] Date of Patent: Aug. 17, 1999

[54] STRAWBERRY PLANT NAMED 'ANA MARIA'

[75] Inventors: Bruce D. Mowrey, La Selva Beach; JoAnne F. Coss, Salinas; Amado Q. Amorao, Camarillo; Larry T. Kodama, Freedom; Joseph I. Espejo, Jr., Watsonville; Thomas M. Sjulin, Aromas, all of Calif.

[73] Assignee: Driscoll Strawberry Associates, Inc., Watsonville, Calif.

[21] Appl. No.: 08/958,715

[22] Filed: Oct. 29, 1997

[51] Int. Cl.[6] ..... A01H 5/00

[52] U.S. Cl. ..... Plt./209

[58] Field of Search ..... Plt./48, 49, 208, Plt./209

*Primary Examiner*—Howard J. Locker
*Assistant Examiner*—Ashwin Mehta
*Attorney, Agent, or Firm*—Pennie & Edmonds LLP

[57] ABSTRACT

This invention relates to a new and distinct variety of strawberry plant named 'Ana Maria', botanically identified as *Fragaria×ananassa*. The closest known variety is 'Key Largo'. The new variety is a partially everbearing fruit bearing variety. The variety is distinguished from 'Key Largo' by its strong plant vigor, slightly concave to flat cross section of the leaf, medium to strong leaf blistering, obtuse to rounded teeth on the terminal leaflet, outward pose of the petiole hairs, smaller to the same size diameter of the calyx relative to the corolla, narrow to medium width of the band on the fruit without achenes, strong fruit glossiness, weak to medium adherence of the calyx to the fruit, fruit of soft to medium firmness, medium to late time of flowering and late harvest maturity.

4 Drawing Sheets

BACKGROUND OF THE INVENTION

The new variety of strawberry was selected in a controlled breeding plot in a cultivated area on the Fly Ranch in Monterey County, Calif., U.S.A., on or about May 1993. The new variety originated as a result of a controlled cross between the strawberry plants named 'Key Largo' (U.S. Plant Pat. No. 8,649) and the strawberry variety named 'Q1' (an unpatented Driscoll selection) in an on-going breeding program. The seedling of the new variety was grown and asexually propagated by stolons at the nursery of Driscoll Strawberry Associates, Inc. in McArthur, Shasta County, Calif. Propagules from the original seedling were tested at the Driscoll Strawberry Associates, Inc. Research Ranch in Monterey County, Calif. (The new variety was further asexually propagated and extensively tested.) This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denominaton of the new variety is 'Ana Maria' (formerly known as 'Anna Maria'). The variety is botanically identified as *Fragaria×ananassa*. Among the characteristic which distinguish the new variety from other varieties of which we are aware are a combination of traits which include plant vigor, the shape of the cross section of the leaf, leaf blistering, shape of the teeth of the terminal leaflet, pose of hairs of the petiole, diameter of the calyx relative to the corolla, the band without achenes on the fruit, fruit glossiness, adherence of the calyx to the fruit, firmness of the fruit flesh, time of flowering and harvest maturity.

COMPARISON TO CLOSEST VARIETIES

The variety which we believe to be closest to 'Ana Maria' from those known to us is 'Key Largo' (U.S. Plant Pat. No. 8,649). There are several characteristics of the new variety that are different from, or not possessed by 'Key Largo'. For example, the plant vigor of 'Ana Maria' is strong, while that of 'Key Largo' is weak to medium. The cross section of the leaf shape of 'Ana Maria' is slightly concave to flat while that of 'Key Largo' is concave. The leaf blistering of 'Ana Maria' is medium to strong while that of 'Key Largo' is weak to medium. The shape of the teeth of the terminal leaflet of 'Ana Maria' is obtuse to rounded while that of 'Key Largo' is acute to obtuse. The pose of the petiole hairs of 'Ana Maria' is outwards while those of 'Key Largo' is upwards. The diameter of the calyx relative to the corolla of 'Ana Maria' is smaller to the same size while that of 'Key Largo' is larger. The band without achenes of the fruit of 'Ana Maria' is narrow to medium while that of 'Key Largo' very narrow to narrow. The fruit glossiness of 'Ana Maria' is strong while 'Key Largo' is weak to medium. The adherence of the calyx of 'Ana Maria' is weak to medium while that of 'Key Largo' is medium to strong. The fruit of 'Ana Maria' is soft to medium in firmness while the fruit of 'Key Largo' is firm. The time of flowering of 'Ana Maria' is medium to late while that of 'Key Largo' is early. The harvest maturity of 'Ana Maria' is late while that of 'Key Largo' is early.

Regarding isozyme analysis, the phosphoglucoisomerase (PGI) isozyme banding pattern for 'Ana Maria' and 'Key Largo' is A1. The leucine aminopeptidase (LAP) isozyme banding pattern for 'Ana Maria' and 'Key Largo' is B3. The phosphoglucomutase (PGM) isozyme banding pattern for 'Ana Maria' and 'Key Largo' is C4. All isozyme analyses were conducted using leaf tissue. See *J. Amer. Soc. Hort. Sci.* 106:684 (1981).

TABLE 1

Isozyme Phenotypes for 'Ana Maria' and 'Key Largo'

| | Cultivar | |
|---|---|---|
| Locus | 'Ana Maria' | 'Key Largo' |
| PGI | A1 | A1 |
| LAP | B3 | B3 |
| PGM | C4 | C4 |

'Key Largo' isozyme data from U.S. Plant Pat. No. 8,649

BRIEF DESCRIPTION OF THE ILLUSTRATIONS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
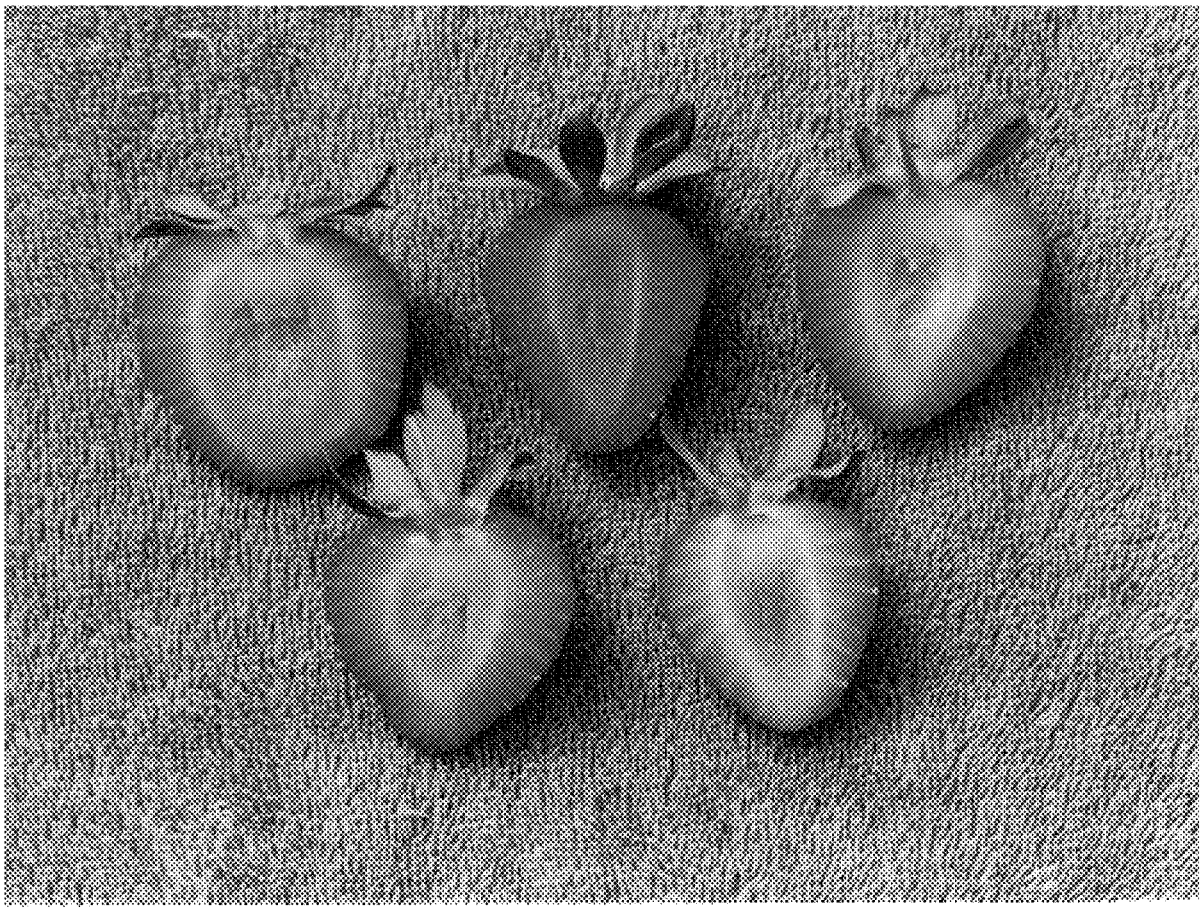
FIG. 1 shows the fruit in longitudinal section, illustrating the typical flesh and flesh coloration.
Figure 2:
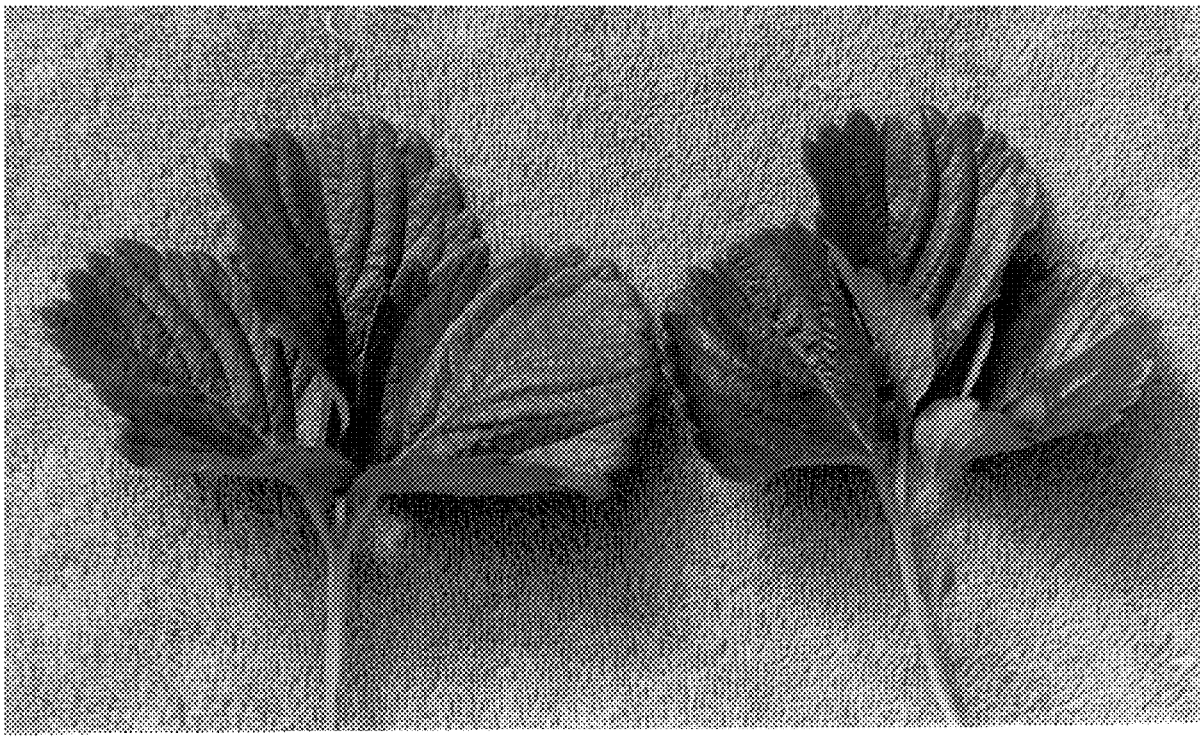
FIG. 2 shows the upper surface of two typical folioles of the new variety.
Figure 3:
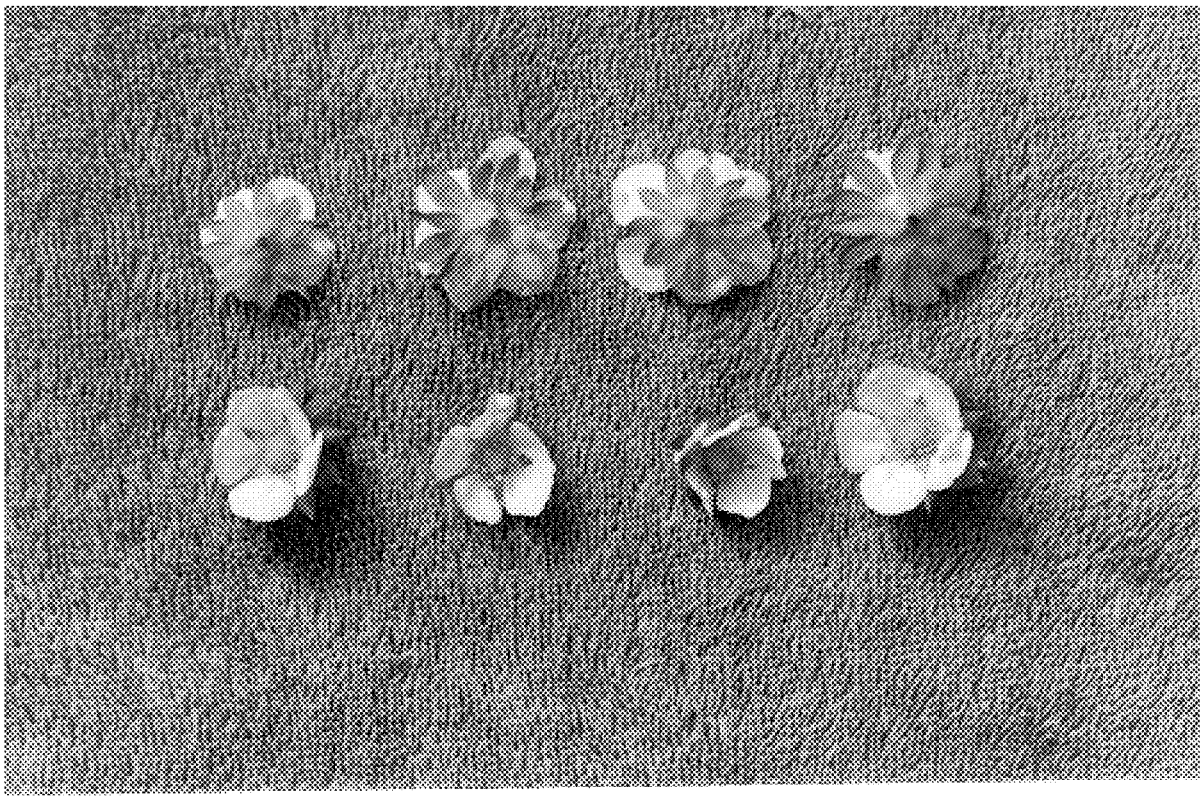
FIG. 3 shows the flower and reproductive organs of the new variety, as well as the size and position of the petals and sepals and the underside of the calyx.
Figure 4:
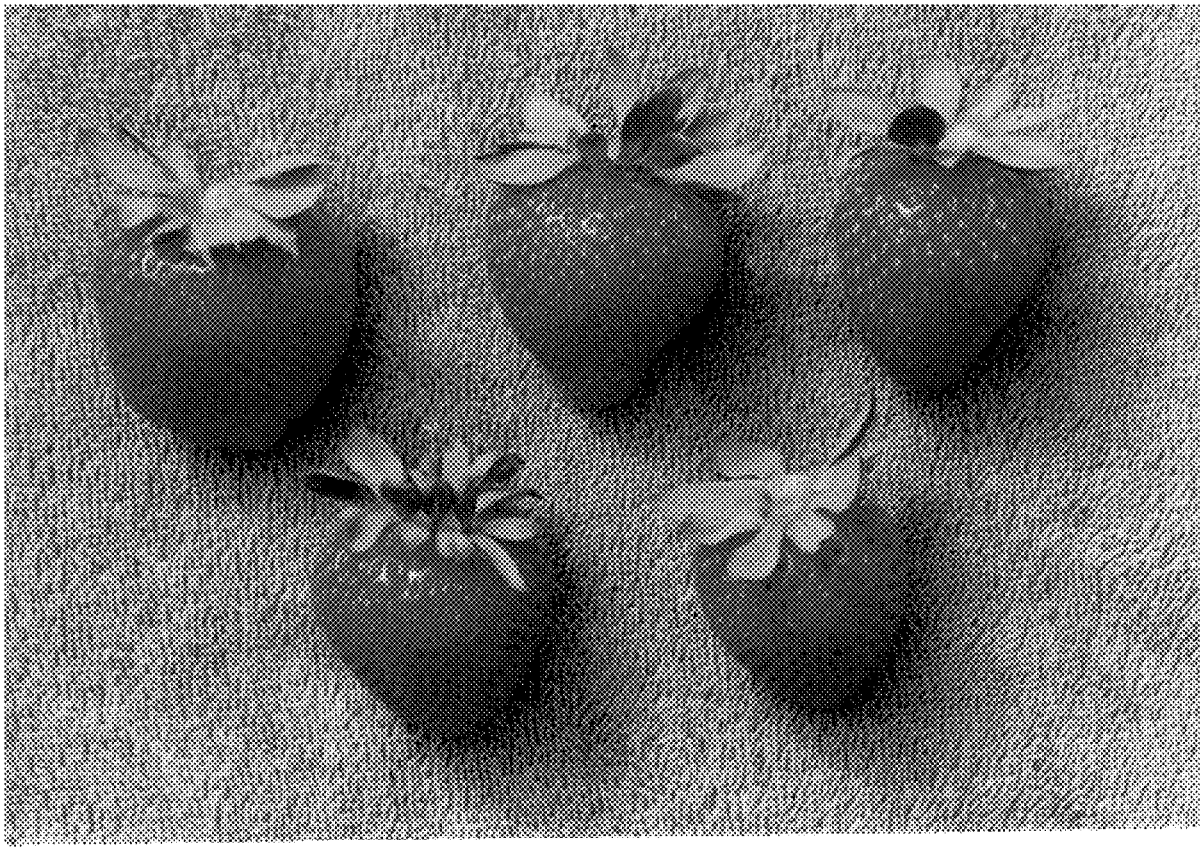
FIG. 4 shows typical whole fruit.

The following detailed description of the new variety is based upon observations taken of plants and fruit grown in experimental test plots of the Driscoll Strawberry Associates, Inc. Research Ranch in Monterey County, Calif., U.S.A. The plant material was planted in the Fall of 1996 and grown in a forcing system. Observations of 'Ana Maria' and 'Key Largo' were taken in a side-by-side comparison under similar conditions. In 1997, 'Ana Maria' was first harvested the week of April 12. The last harvest occurred the week of November 3. Additional observations were taken of plants grown in the Watsonville/Salinas area during the 1998 growing season. These harvest dates are for the Driscoll Strawberry Associates, Inc. Research Ranch in Pajaro, Monterey County, Calif. This description is in accordance with UPOV terminology. Color designations, color descriptions, and other phenotypical descriptions may deviate from the stated values and descriptions depending upon variation in environmental, seasonal, climatic and cultural conditions. Colors are described using standard Munsell Notation.

Propagation

The new variety is principally propagated by way of stolons. Although propagation by stolons is presently preferred, other known methods of propagating strawberry plants may be employed.

Characteristics of the New Variety

The following information is provided to describe the new variety.

Plant:

*Habit.*—Globose to upright.

*Density.*—Medium to open. Specifically, the average height and diameter of the foliage at fruiting are 29.2 cm and 49.1 cm, respectively.

*Vigor.*—Strong.

Foliage:

*Leaf.*—Color — upperside — medium green, 1.4G 2.1/4.4. The underside of the leaves are gray-green which is not included in the Munsell color cascade. Shape in cross section — slightly concave to flat. Blistering — medium to strong. Number of leaflets — three only. Leaf glossiness — medium.

*Terminal leaflet.*—Margin profile — flat. Length to width ratio — longer than broad. Shape of base — rounded to slightly oblique. Shape of teeth — obtuse to rounded. The average terminal leaflet length and width is 8.3 cm and 8.1 cm, respectively. The terminal leaflet length/width ratio is 1.03.

*Petiole.*—Pubescence — sparse. Pose of hairs — outwards. The average petiole length is 23.7 cm. The Munsell color rating for the petiole color is 3.7GY 6.0/10.7.

*Stolons.*—Number — few to a medium number. Anthocyanin coloration — medium. Thickness — thin to medium. Pubescence — sparse to medium.

Inflorescence: Position relative to foliage — level with to above.

Flower:

*Size.*—Small to medium. 'Ana Maria' has an average flower diameter of 27.8 mm with a range from 21 mm to 35 mm.

*Diameter of calyx relative to corolla* (*on secondary flowers*).—Smaller to same size.

*Diameter of inner calyx relative to outer* (*on secondary flowers*).—Smaller to the same size.

*Spacing of petals* (*on secondary flowers with* 5 *or* 6 *petals*).—Free to touching.

*Petal color.*—White (White is not referenced on the "Munsell Color Cascade").

*Petal length to width ratio* (*on secondary flowers*).—As long as broad.

*Flower fragrance.*—Not fragrant.

Fruiting truss:

*Attitude at first picking.*—Semi-erect.

*Length.*—Long.

Fruit (secondary fruit on one year old plants): Strawberry plants possess a branching inflorescence, or peduncle, having a primary (first) flower which is the largest and secondary flowers which are on the lateral branches. The average length of the peduncle and influorescence are 11.7 cm and 30.8 cm, respectively. The peduncle color is 3.3Gy 5.0/8.8. "Secondary Fruit" are those that develop from secondary flowers which develop from lateral buds on the peduncle. One year old plants are those which are in their first year in the fruiting fields.

*Ratio of length to maximum width.*—As long as broad to longer than broad.

*Size.*—Medium. The average weight of the fruit is 19.6 g/berry.

*Predominant shape.*—Conical.

*Difference in shapes between primary and secondary fruits.*—None or very slight. The average length and width of the primary fruit are 44 mm and 39 mm, respectively. The length/width ratio of the primary fruit is 1.15. The average length and width of the secondary fruit are 35 mm and 31 mm, respectively. The length/width ratio of the secondary fruit is 1.14.

*Band without achenes.*—Narrow to medium.

*Unevenness of surface.*—Weak.

*Skin color.*—Dark red (7.5R 2.1/6.1) Fruit color in the photographs may vary from the Munsell color rating due to photographic or reproduction error.

*Evenness of color.*—Even.

*Glossiness.*—Strong.

*Insertion of achenes.*—Level with surface.

*Insertion of calyx.*—Level with to set above the fruit.

*Pose of the calyx segments.*—Spreading.

*Size of calyx in relation to fruit diameter.*—Same size to larger.

*Adherence of calyx.*—Weak to medium.

*Firmness of flesh* (*when fully ripe*).—Soft to medium.

*Color of flesh.*—Medium red (6.8R 4.6/16.5).
*Evenness of color of flesh.*—Slightly uneven.
*Distribution of flesh color.*—Marginal and central.
*Hollow center.*—Small.
*Sweetness.*—Medium to strong.
*Texture when tasted.*—Fine to medium.
*Acidity.*—Medium.
*Fragrance.*—Ripe fruit of 'Ana Maria' are very aromatic with a fragrance typical of ripe strawberries.

Time of flowering (50% of plants at first flower): Medium to late. The average length of time from flowering to harvest is 26.4 days and ranges from 23 to 28 days.

Harvest maturity (50% of plants with ripe fruit): Late.

Type of bearing: Partially everbearing. Partially everbearing varieties will continue to re-flower and fruit under cool conditions, such as those that occur in Coastal California. These varieties stop flowering under warm conditions. 'Ana Maria' has excellent shelf-life with 70% of the fruit possessing little or no storage damage in shelf-life evaluations. 'Ana Maria' produces ample pollen and is self-fertile.

Resistance to Stress

The new variety is moderately resistant to high pH, high soil salt levels, drought and high temperatures.

Disease Resistance and Susceptibility

The 'Ana Maria' variety is moderately susceptible to *Xanthomonas fragariae*. 'Ana Maria' is moderately resistant to Powdery mildew and Botrytis fruit rot.

The 'Ana Maria' variety is susceptible to injury by the two-spotted spider mite (*Tetranychus urticae*), *Tarsonemus pallidus, Aphelencoides fragariae,* and lygusbug (*Lygus hesperus*).

What is claimed is:

1. A new and distinct variety of strawberry plant, substantially as shown and described.

* * * * *